United States Patent [19]

Rueter et al.

[11] Patent Number: 5,824,019
[45] Date of Patent: *Oct. 20, 1998

[54] PACING SYSTEM WITH PHYSIOLOGICALLY TIMED VENTRICULAR PACING

[75] Inventors: John C. Rueter, Shoreview; Catherine R. Condie, Minneapolis, both of Minn.

[73] Assignee: Medtronic, Inc., Minneapolis, Minn.

[*] Notice: This patent issued on a continued prosecution application filed under 37 CFR 1.53(d), and is subject to the twenty year patent term provisions of 35 U.S.C. 154(a)(2).

[21] Appl. No.: 729,465

[22] Filed: Oct. 11, 1996

[51] Int. Cl.$^6$ .................................................. A61N 1/365
[52] U.S. Cl. ................................................................ 607/17
[58] Field of Search .................................. 607/9, 17–19, 607/24

[56] References Cited

U.S. PATENT DOCUMENTS

| | | |
|---|---|---|
| 4,303,075 | 12/1981 | Heilman et al. . |
| 4,733,667 | 3/1988 | Olive et al. ............................... 607/24 |
| 4,773,401 | 9/1988 | Citak . |
| 5,058,583 | 10/1991 | Geddes et al. ............................. 607/18 |
| 5,235,976 | 8/1993 | Spinelli ..................................... 607/25 |
| 5,334,222 | 8/1994 | Salo et al. .................................. 607/17 |
| 5,340,361 | 8/1994 | Sholder ..................................... 607/24 |
| 5,417,715 | 5/1995 | Noren et al. ............................... 607/9 |
| 5,417,717 | 5/1995 | Salo et al. .................................. 607/18 |
| 5,507,785 | 4/1996 | Deno ......................................... 607/24 |

Primary Examiner—Jeffrey R. Jastrzab
Attorney, Agent, or Firm—Harold R. Patton; Michael B. Atlass

[57] ABSTRACT

There is provided an improved pacing system and method which monitors when the ventricle has become appropriately filled with blood and controls the delivery of each ventricular pace pulse to substantially coincide with desired ventricular filling, e.g., when the chamber has substantially filled. By this technique, the desired time for delivering the ventricular pace pulse is determined on a beat-by-beat basis, providing an improved physiologically optimum mode of pacing. The physiologically ventricular pacing technique of this invention is applicable either to a single chamber pacemaker, or to a dual chamber pacemaker, and in either case enables the important improvement of delivering the pace pulse at the most physiologically appropriate time. In a first embodiment, the moment when the ventricle has substantially filled with blood is determined by monitoring impedance variations which vary inversely with ventricular volume, such that filling of the ventricle corresponds to the time when the impedance waveform bottoms out, or reaches a minimum level. Other sensor arrangements which provide information as to the state of or rate of change of ventricular volume can likewise be used. The invention enables a single lead-single chamber pacemaker which achieves effective synchrony with atrial contractions, or a dual chamber pacemaker which does not require programming of an AV interval.

17 Claims, 4 Drawing Sheets

PACING SYSTEM WITH PHYSIOLOGICALLY TIMED VENTRICULAR PACING

FIELD OF THE INVENTION

This invention relates to cardiac pacing systems and, more particularly, to a pacing system and method for delivering ventricular pace pulses based upon a determination that the ventricle is physiologically ready to be paced.

BACKGROUND OF THE INVENTION

Cardiac pacing systems have been in use for some decades now, and have undergone generations of improvements. Early cardiac pacemakers were single chamber devices, e.g. pacing only the ventricle. Patients with such single chambered pacemakers sometimes exhibited what is called "pacemaker syndrome," a condition of less than optimum cardiac output due to the fact that the ventricle is paced asynchronously with respect to the atrium and is caused to contract when it is not optimally filled with blood. Subsequent pacemaker developments have led to several major improvements. The dual chamber pacemaker, which provides the capability of sensing and also pacing in the atrium as well as the ventricle, enables delivering of ventricular pulses which are synchronized with respect to atrial contractions. Such synchronized pacing more closely simulates the physiology of the normal heart and enables the ventricle to be paced when it is more optimally filled by the contraction of the atrium. While such a dual chamber pacing system, e.g. a DDD system, provides a more optimal timing for delivery of the ventricular pace pulses, there remain certain problems with dual chamber systems which have not been completely solved technically. For example, P wave sensing is not as reliable as sensing the QRS, due to the lower amplitude of the P wave, and also due to the possibility of sensing a far field R wave (FFRS). Much work has been done toward ensuring reliable detection of the P wave, and avoiding oversensing or undersensing, but this adds to the complexity of the pacemaker and the resultant cost. Another area is that of accurately determining the AV interval, i.e., the interval timed out by the pacemaker between detection of a spontaneous atrial beat (P wave) and delivery of a ventricular pace pulse. Again, considerable work has been done in this area, but it is difficult to accurately mimic the heart's natural conduction from the atrium to the ventricle. See, for example, U.S. Pat. No. 5,340,361, which discloses a technique for adjusting the AV interval as a function of the timed interval between a natural P wave and a resulting natural QRS when these signals can be observed. The obvious problem with this solution is that if the patient's conduction system is faulty, which probably is the premise for the patient having a pacemaker, then the natural AV interval cannot readily be checked.

Another substantial improvement in pacing systems, which was introduced at least by the early 1980's, is that of the rate-responsive pacing system. A rate responsive pacemaker utilizes one or more sensors for sensing a selected patient parameter or parameters, which parameters contain information reflective of the patient's desired physiological heart rate. Using this parameter information, the pacing rate is automatically and continuously adjusted. Thus, a VVI pacemaker, which paces and senses only in the ventricle, becomes a VVIR pacemaker when it is also rate responsive; a DDD pacemaker similarly becomes a DDDR pacemaker, with the capability of adjusting the pacing rate for both the atrial and ventricular pace pulses. Some early versions of such rate responsive pacemakers which were single-chamber implementations, and which did not provide any synchrony between an atrial spontaneous beat and a ventricular pace pulse, might have actually exacerbated pacemaker syndrome in patients, due to pacing the ventricle when it was not optimally filled. Nonetheless, the rate responsive mode does provide a significant improvement, even though it does not precisely mimic the patient's heart in terms of delivering the ventricular stimulus when the ventricle has been optimally filled by the atrial contraction. Rate responsive pacemakers have utilized such parameters as activity, Q–T interval, blood oxygen, intra-cardiac pressure, and impedance measurements within the ventricle. See, for example, U.S. Pat. No. 4,773,401, which utilizes an impedance waveform to get a measure of contractility, which measure is used as a control parameter for controlling pacing rate; and U.S. Pat. No. 5,235,976, which uses an impedance measurement to get the heart's "active time," in order to obtain a measure of a safe upper rate limit. In each of these cases, it is pacing rate that is adjusted, but there is no provision for beat-to-beat determination of when the ventricle has been optimally primed for contraction. Thus, while there has been substantial success in adapting the pacing rate to patient needs, such systems have not dealt in any manner with the objective of delivering the ventricular pace pulse at a determined time within the cycle so as to physiologically optimize cardiac output on a cycle-to-cycle basis. While a rate responsive pacemaker may theoretically adjust beat-to-beat time interval each cycle, such adjustment is seen to be made on the basis of a sensed trend in cardiac demand, and is not based upon the actual status of the ventricle following an atrial contraction. Stated another way, rate is only one variable which a pacemaker can change to meet cardiac demand; the exact cycle-to-cycle timing of the ventricular pace pulse is an important factor that needs to be addressed.

Many physicians who implant pacemakers still prefer to use ventricular-only devices, both because they are less expensive, and because implantation does not entail the more difficult procedure of implanting an atrial lead. Single pass leads, such as are employed for VDD systems, have obtained some use but are still broadly considered to be of marginal or questionable effectiveness. Thus, there is no system or methodology that has been demonstrated to be effective for implementing a single chamber ventricular-only device which is "aware" of the status of the ventricle in terms of being filled following an atrial contraction. What is highly desired, and thus far unavailable, is a pacing system which would require only a single unipolar or bipolar pacing lead, and would pace and sense only in the ventricle, but yet be able to obtain information as to when the ventricle has substantially filled with blood so as to optimally time the ventricular pace pulse. Note that while the filling of the ventricle is primarily due to the atrium, part of the filling is due to ventricular relaxation. Thus, even in the presence of a largely ineffective atrium, e.g., from atrial fibrillation, the ventricle can be paced when it has been substantially filled. Such a system would have all of the advantages of a simple single chamber pacemaker system, but would be superior to a VVI or even VVIR pacing system in that it would avoid pacemaker syndrome, and would be truly physiologic in terms of providing accurate synchronous pacing with regard to the filling of the ventricle by the atrial contraction. One might to designate a VVI pacemaker which includes this Physiologic feature as VVIP, and a VVIR pacemaker which includes this Physiologic feature as VVIR/P. Similarly, a DDD pacing system which uses this invention may be designated DDDP; a DDDR system would be a DDDR/P.

The present invention provides such an improved ventricular physiological pacing system by detecting when the ventricle has substantially filled with blood, usually following an atrial contraction, and basing the timing of the delivered ventricular pace pulse upon such detection. A study of ventricular lead impedances, i.e., intra-ventricular impedance, in humans with dual chamber pacemakers has shown that such intra-ventricular impedance is a function of the degree of filling of the ventricle. It is seen that the variation of intra-ventricular impedance is a function of proper AV intervals in dual chamber pacers, and varies significantly in single chamber pacers as a function of whether or not the ventricular pace happens to be at an appropriate time with respect to the atrial contraction. Simply stated, we have observed an inverse relationship between intra-ventricular impedance and the degree to which the ventricle is filled with blood, namely that such impedance drops as the ventricle is filled with blood and reaches a minimal level when it is substantially filled. We have observed studies of the intra-ventricular signals used to implement Minute ventilation-style rate response in a pacemaker. In these studies, measurements are made at short intervals approximating nearly continuous measurement of the intra-ventricular impedance. The signals show that ventricular impedance is lowest at a time corresponding to the ventricle being filled with blood. In unmoderated VVI systems where this signal was recorded, the continuous signals show wide variations, which we believe are related to ventricular pace events which are asynchronous to atrial filling.

It has also been found that ventricular lead impedance, i.e., the impedance to a delivered ventricular pace pulse, varies significantly with the AV delay, in correspondence with the variation of intraventricular impedance. Thus, we observe that at a short AV interval such as 30 ms the ventricular lead impedance is significantly higher than at an AV delay such as 150 ms. Further, once a substantial minimum lead impedance is reached, further lengthening of the AV interval does not further lower the ventricular lead impedance. As above, the physiological explanation for this appears to be that there is less blood in the ventricle after the short AV interval, making the pathway across which the lead impedance is measured less conductive (since blood is about 3 times as conductive as general body tissue).

In accordance with these observations, it is an object of the present invention to provide a pacing system which delivers more physiologically timed ventricular pace pulses by monitoring at least one sensed parameter indicative of the level or degree of filling of the ventricle, and controlling delivery of each ventricular pace pulse to correspond to determined optimally filled state of the ventricle, thereby providing an improved physiological response.

SUMMARY OF THE INVENTION

In accordance with the above object, there is provided a pacing system and method of pacing which provides an improved physiological response by coordinating, on a beat-to-beat basis, the delivery of a ventricular pace pulse with the substantial filling of the ventricle following an atrial contraction, whereby the ventricle is paced and caused to contract at a time each cycle when the ventricle has just been optimally filled with blood. The pacing system includes, in the case of single chamber ventricular pacemaker, a pulse generator for generating ventricular pace pulses and a lead with at least one pacing electrode positioned at the distal end of the lead for ventricular pacing. An oscillator generates a high frequency impedance-measuring signal, preferably limited to either the period of time each cycle when impedance is undergoing significant change, or to times expected to yield the most useful result. In a first embodiment, the lead also has at least one electrode for receiving the impedance-measuring high frequency signal from the pacemaker, and one or two electrodes which are utilized for detecting a measure of the high frequency signal, thereby providing an impedance measurement in a known fashion. The pacemaker has logic circuitry for monitoring and detecting when the impedance reflects that the ventricular volume has increased due to being filled with blood to a substantially minimum value, thereby indicating the optimum time for delivering a ventricular pace pulse. When the optimum time is determined, the pacemaker control controls the ventricular pulse generator to deliver the ventricular pace pulse. For a single chamber ventricular pacemaker, this system provides for a VVIP mode of pacing. The invention is also applicable to a pacemaker which includes rate response, thereby providing a VVIR/P mode of operation. The invention is likewise applicable to optimizing the time of ventricular pace pulse delivery in a dual chamber or DDD-type pacemaker, in which case there is provided either a DDDP or DDR/P mode of operation. Either the single chamber or dual chamber embodiment provides the additional advantage that AV delay need not be programmed by the physician at time of implant, or re-programmed subsequently.

However, it should be noted that the inventive concept enabled here to allow for pacing based on the filling of the ventricle can be applied to any single or multi chamber pacing device and adaptations and improvements can be made to incorporate this idea into any pacing or diagnostic or even data gathering scheme or device in which it would be useful to know or use this data. Nor should the application be limited to single lead devices, since information gathering and stimulation functions can be provided through other leads in cooperation with the inventive concepts taught herein.

In a preferred embodiment, the pacemaker includes an algorithm which monitors cycle-to-cycle variation of intraventricular impedance, and determines a desired time for pace pulse delivery based on a selected evaluation of impedance change. The pacemaker algorithm can work in different ways, within the scope of the invention: it can detect of a drop of impedance by a predetermined amount from a high level established following the last delivered pace pulse; it can detect when the impedance drops below a predetermined threshold; it can detect the absolute impedance minimum by examining to see when the derivative of impedance with respect to time goes to zero; it can detect when impedance drops below a threshold which is based on a rolling average of prior impedance minima; and alternatively it can base the detection on a timing window which tracks when prior minima have occurred.

In yet another embodiment, the pacemaker watches for a certain amount of impedance change within a certain time. Thus, a steep slope of sufficiently long duration indicates that the ventricle is filling, but not yet filled. After detecting such a slope, the pacemaker anticipates the desired time of pacing, and waits a short interval to deliver the pace pulse. This enables pacing at a moment before the ventricle is fully filled, which may be desired for a patient where stretching the ventricular tissue could lead to hypertrophy. Such an "anticipatory" algorithm has the further advantages of providing time to set up delivery of the pace pulse, and enabling shut off of the the oscillator which generates the high frequence impedance measuring signal, in advance of the pulse delivery.

Although the preferred embodiment as illustrated uses impedance measurement to determine when the ventricle has filled, other techniques for sensing the filling of the ventricle with blood can be used to make this determination.

DETAILED DESCRIPTION OF THE PREFERRED EMBODIMENTS

Figure 1:
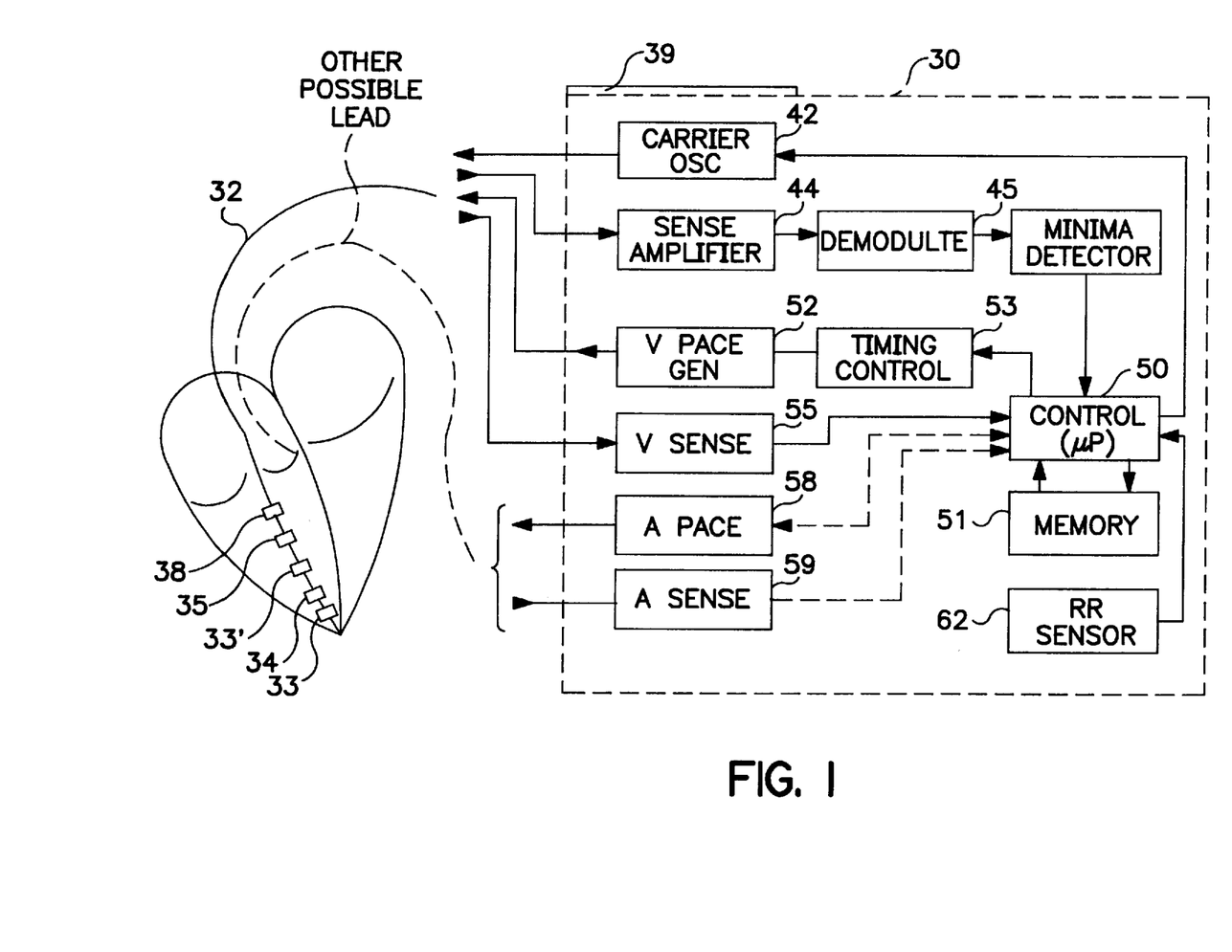
FIG. 1 is a system diagram showing the major components for carrying out the physiological ventricular pacing in accordance with this invention.

Referring now to FIG. 1, there is shown a system block diagram which shows the primary components of a ventricular physiological pacemaker in accordance with this invention. A pacemaker, indicated by dashed block 30, suitably an implantable pacemaker, combines with a lead 32 for providing pacing pulses to the patient. Lead 32 has a plurality of conductors leading from its proximal end where it connects to pacemaker 30, to plural electrodes, as illustrated. The electrodes are positioned toward the distal end of the lead for positioning within the patient's right ventricle. An electrode 33 is shown at about the distal tip, which can be used in combination with the pacemaker can 39, for unipolar pacing, or in combination with electrode 33 for bipolar pacing. A pair of impedance sense electrodes are positioned as shown at 34, 35, for sensing the voltage drop across the interelectrode distance, which voltage is a measure of the intra-ventricular impedance when a constant current of predetermined magnitude is passed through the ventricle. Such a current is provided from carrier oscillator 42, and suitably passed between tip electrode 33 and the most proximal electrode indicated at 38. This technique of measuring intra-ventricular impedance is well known in the art; by way of example, it is illustrated in U.S. Pat. No. 5,417,717. Thus, for the system as illustrated, and for bipolar pacing, lead 32 comprises five conductors which connect from its proximal end which is connected to pacemaker 30, to the respective electrodes 33, 33 , 34, 35 and 38 which are positioned in the ventricle. Of course, the lead can have fewer conductors, as would be possible with a unipolar system, or with a system that used the pacing delivery electrodes for intraventricular impedance.

Figure 2A:
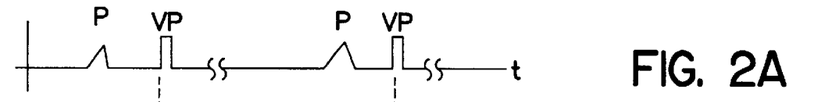
FIGS. 2A, 2B and 2C present a series of timing diagrams illustrating how a delivered ventricular pace pulse is related to impedance measurement.
Figure 2B:
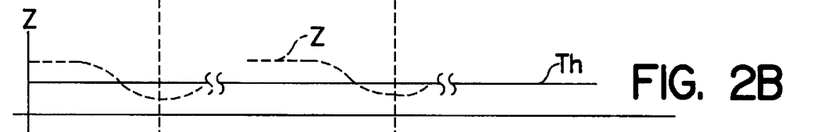
Figure 2C:
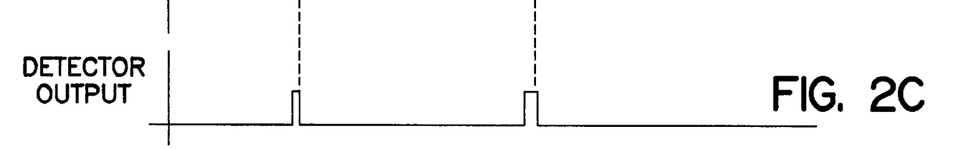

Carrier oscillator 42 is controlled by control block 50, which suitably includes a microprocessor, to provide a high frequency carrier at constant current, which high frequency current is sub-threshold and is delivered between pace pulses. Oscillator 42 is suitably controlled to generate pulses of current at intervals which are sufficiently short so that an effectively continuous measurement of impedance (Z) is obtained. Additionally, energy can be saved by controlling the impedance-measuring current only for a limited period, or window of time during which there are significant impedance variations, i.e., when impedance starts to drop from a maximum value, down to where the minimum occurs, as illustrated at T in FIG. 2B. The sensed voltage at electrodes 34, 35 is connected to sense amplifier 44, the output of which is filtered and demodulated at block 45, to provide a time waveform representative of the change of impedance within the right ventricle. FIG. 2B presents an illustration of how this impedance is at a relatively high level until about when the atrium contracts, as indicated by the symbol P in FIG. 2A, following which the impedance decreases to a minimum value, corresponding to the filling of the ventricle with blood. A minima detector 46 detects a measure of when the impedance drops to its minimum, e.g. when it passes below a threshold Th as indicated in FIG. 2B. The minima detector can, in such a simple application, be strictly a hardware detector; or, alternately, the demodulated signal for 45 can be transformed into a digital signal, and the minima detection can be software controlled. Thus, the minima detector as illustrated at 46 may be a separate hardware circuit, or it may be part of the control block illustrated at 50. Several ways of determining when an effective impedance minimum has been reached, and for triggering detector output as illustrated at FIG. 2C, are discussed in greater detail hereinbelow.

Still referring to FIG. 1, a ventricular pace generator 52 delivers ventricular pace pulses between a first electrode 33, and either a second electrode 33 for bipolar pacing or pacemaker can 39 for unipolar pacing. Pace generator 52 is controlled by timing control 53, which in turn controlled by the microprocessor control illustrated at block 50. The control circuit at 50 suitably utilizes memory as shown at 51, where data or software instructions can be stored. Although not shown, it is to be understood that commands or new control data can be transmitted from an external programmer source to memory 51, in a conventional fashion.

Still referring to FIG. 1, the signals sensed across electrodes 33, 33 or 33,39 are inputted to V sense block 55, the output of which is connected through to control block 50. This enables conventional "demand" operation, whereby generation of a pace pulse is disabled if a timely spontaneous QRS has been detected. Control circuit 50 thus handles all of the pacemaker timing, as is conventionally done, controlling generation of ventricular pace pulses both as a function of whether there has been a spontaneous ventricular signal sensed, and as a function of the monitoring of the impedance signal and detection of an impedance minimum. Additionally, the pacemaker may contain one or more rate responsive sensors as shown at block 62, the outputs of which are connected to control block 50 and used in a conventional manner to control pacing rate.

Figure 3:
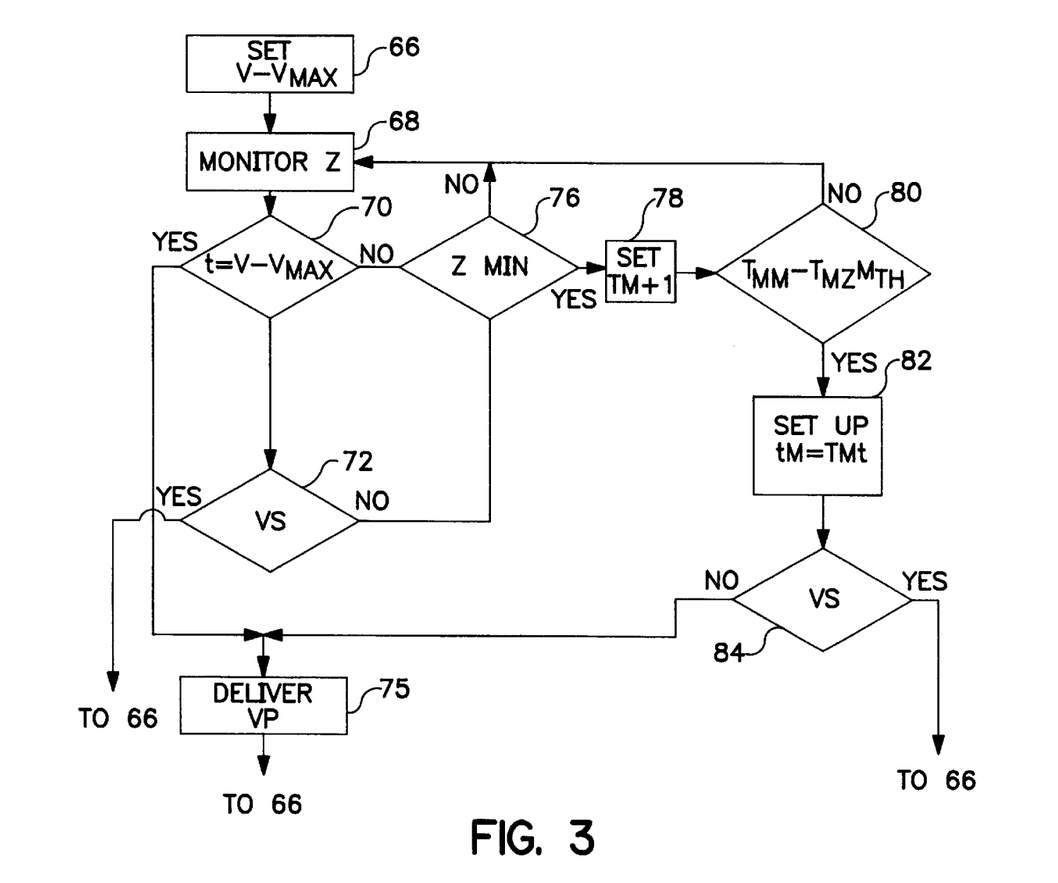
FIG. 3 is a flow diagram illustrating the primary steps of the method of this invention.

Referring now to FIG. 3, there is shown a generic flow diagram for achieving VVIP pacing in accordance with this invention. This flow diagram illustrates only the primary steps necessary to achieve the improvement of pacing when the ventricle is optimally filled to a desired level, and does not represent all other control steps which are conventional in modem pacemakers.

Starting at block 66, the escape interval $(V-V)_{max}$ is set corresponding to the programmed pacing rate, or as adapted by a rate responsive feature. Thus, at the start of the ventricular based cycle, the escape interval is set and timeout of $(V-V)_{max}$ is initiated in the normal manner. As illustrated at block 68, the intra-cardiac impedance Z is monitored. While this monitoring is going on, the pacemaker is also continually determining whether the escape interval has timed out, as illustrated at 70, or whether a spontaneous ventricular sense (VS) has been found, as illustrated at 72. If the escape interval has timed out, the algorithm branches to block 75, where a ventricular pace is delivered; note that in this instance, an impedance minimum has not yet been detected; the pacemaker does not wait, but proceeds to deliver the pace pulse. At 72, if a spontaneous QRS has been sensed, this ends the cycle and the program returns to block 66 to start the next cycle. Assuming that there has been no VS and no timeout of the escape interval, the algorithm continually looks at Z to see if it has dropped to minimum impedance ($Z_{min}$), as indicated at 76. Several illustrative techniques for finding $Z_{min}$ are described in more detail in connection with the flow diagrams of FIG. 4. If $Z_{min}$ has not been found, the pacemaker continues to monitor Z. However, when a measure of $Z_{min}$ has been found, the routine branches to block 78, where it stores a value corresponding to the time of detecting $Z_{min}$, $T_{M+1}$. Following this, at block 80 the pacemaker compares the value of $T_{M+1}$ with the time of the last minimum detection, $T_M$. If, but only if the difference is greater than a predetermined minimum ($M_{th}$), then the routine branches to block 82; if not, the routine continues to monitor impedance until a yes response is found at block 70, 72, or 80. Thus, block 80 provides the equivalent of a high rate limit, and protects against impedance minima determinations which would lead to too high a ventricular pacing rate. At block 82, control of the ventricular pace pulse (VP) is set, and $T_M$ is set equal to $T_{M+1}$. The ventricular pace pulses may be delivered immediately upon detection of $Z_{min}$ or may be delayed by a small period of time, if the physician desires such in order to avoid a hypertrophy situation. Alternately, as discussed below in connection with FIG. 5, it may be desirable to advance delivery of VP before the ventricle is completely filled. Thus, while the moment of reaching minimum impedance might represent an optimum AV interval for many hemodynamic purposes, it may be advisable to delay or advance delivery of the pace pulse for other purposes which are related to the patient's particular conditions. At block 84, the routine again tests to see whether there has been a ventricular sense (in the case of a delay after detection of $Z_{min}$), and exits back to the beginning of the routine if there has been a ventricular sense. Assuming no VS at 84, the pacemaker then proceeds to deliver a VP at block 75.

Figure 4A:
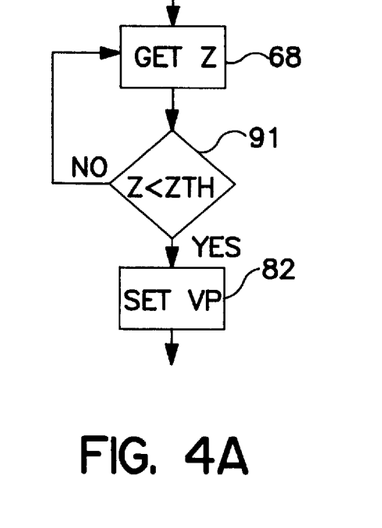
FIGS. 4A, B and C are respective flow diagrams illustrating algorithms for detecting when measured, impedance indicates that the ventricle is substantially filled, such that it is physiologically primed for being paced.

Referring now to FIG. 4A, there is shown a first simple flow diagram for obtaining a measure of Z indicative of when the ventricle has substantially filled with blood. At 68, the impedance value is obtained. At block 91, the value of the impedance is compared with a threshold value designated $Z_{th}$. If Z is not less than $Z_{th}$, the routine simply returns to get a next value of Z, and continues to make the comparison until Z is found to have dropped below $Z_{th}$. The loop frequency, or time interval between sampling Z and making the comparison, can be synchronized to the carrier pulses from oscillator 42, or may be set by software at any rate sufficient to provide the required timing accuracy. After the impedance value has been found to drop below the threshold value, the routine goes to block 82 and sets control for delivery of a ventricular pace pulse (VP). At 83, the value of the time interval between the last VP and the current VP (V—V) is stored, and the time of the next measurement is set. Thus, the pacemaker can wait n cycles before measuring Z again, using the stored V—V time. Or, the determination can be made every cycle. Suitably, no next impedance measurement is made until some predetermined time interval after the ventricular pace has been delivered, to allow the Z level to be re-established at its relatively high level corresponding to an empty ventricle.

Figure 4B:
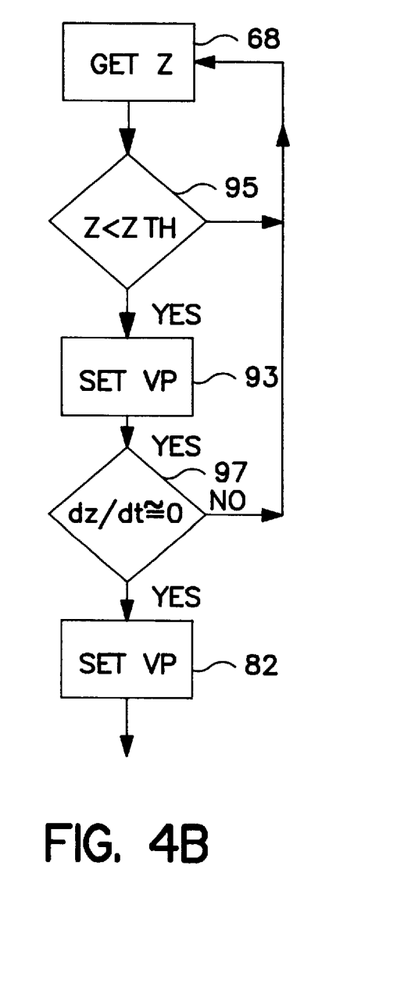

Referring to FIG. 4B, there is shown an alternate algorithm for determining when to deliver the pace pulse. After getting the impedance value at 68, it is compared to a predetermined $Z_{th}$ as shown at 95. However, in this case, after the impedance value has dropped below the threshold value, the routine goes to block 96 and inspects the time derivative, dZ/dT. Then, at 97 the dZ/dT is evaluated to see whether it is zero, i.e., whether the impedance value has reached a minimum which indicates that the ventricle has filled with blood. If no, the routines loops back to 68; if yes, it goes on to set the ventricular pace pulse, as illustrated at 82.

Figure 4C:
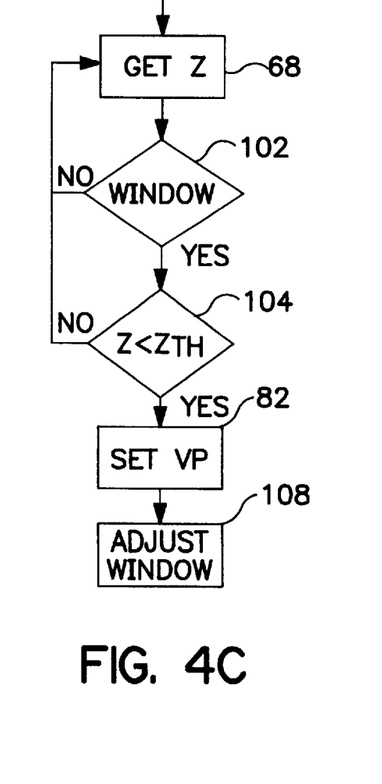

Referring to FIG. 4C, there is shown another embodiment which utilizes a timing window. The timing window may be, for example, 10–50 ms, and is an adjustable window of time during which the pacemaker looks to see if impedance has dropped below a predetermined threshold. After getting the impedance value at 68, the routine looks to see whether the window is operative. If no, the routine loops back to 68; if yes, it goes to block 104 and determines whether the impedance has dropped below a predetermined threshold. When the answer at 104 is yes, the routine proceeds to set the control for delivery of a ventricular pace pulse, and then adjusts the window at 108 in accordance with the time that the impedance has been found to drop below the threshold. Thus, in a given cycle, if the time that impedance has been found to drop below threshold is later than a stored value of the center of the window, the window is adjusted by a small increment to a later time; if the time of reaching threshold is sooner, the window is adjusted to a sooner time.

Figure 5:
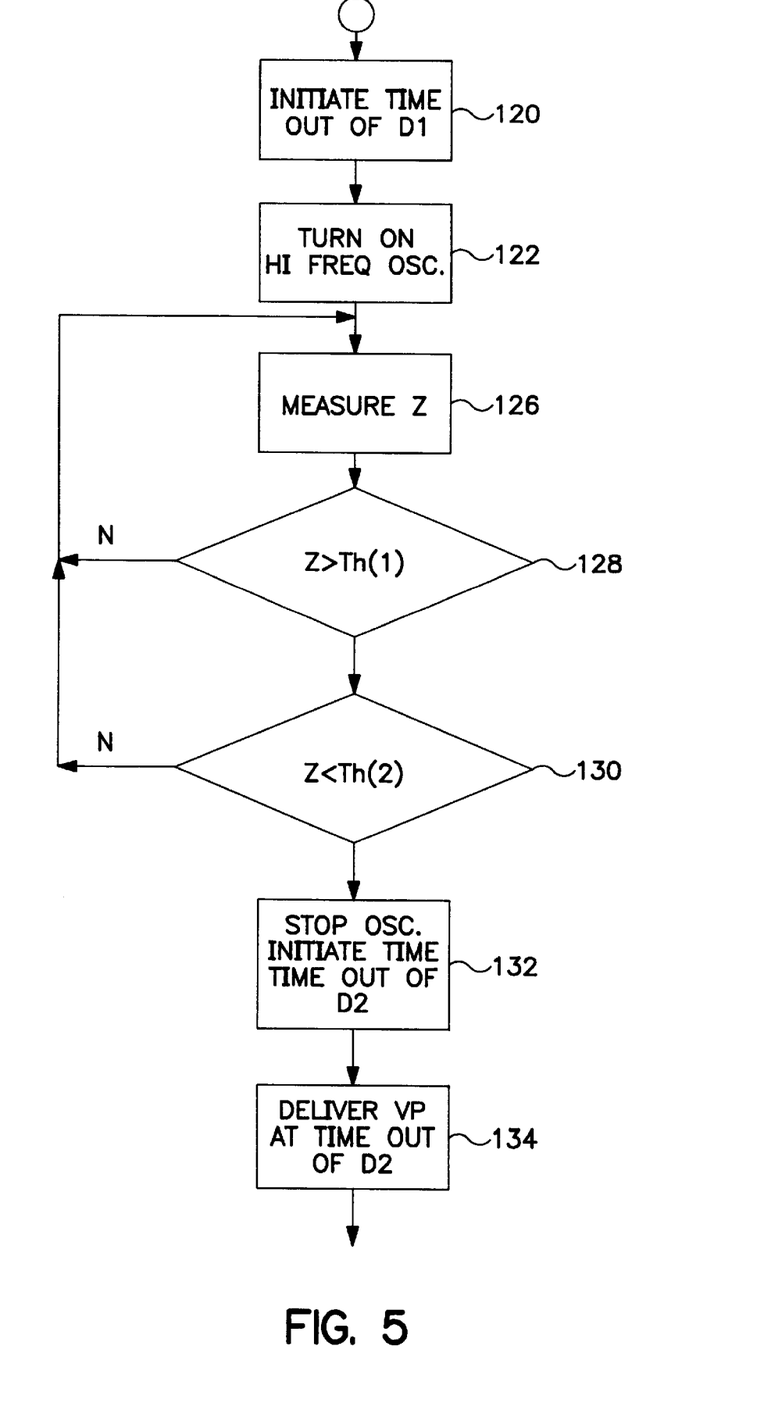
FIG. 5 is a flow diagram showing the primary steps of another procedure for determining the physiologically desired time to pace, including the steps of turning the high frequency oscillator on only during a window when impedance is expected to change.

Referring now to FIG. 5, there is shown a flow diagram of another preferred embodiment for carrying out the impedance measurement and also for determining the desired time for delivering the pace pulse. The routine starts following a ventricular event. At 120, the routine sets a timer and waits to timeout at duration D1, which corresponds to an interval following delivery of the last pace pulse (or ventricular sense). The timeout of D1 is the time of re-starting the impedance measurement for the next cycle. D1 may be, for example, 400, but depends on patient conditions. At 122, the high frequency oscillator for the impedance measurement is turned on at the timeout of D1. Following this, at 126, impedance measurements are taken. At 128 the pacemaker checks to see if impedance is greater than a first predetermined threshold, Th(1), which is a value set to be below the normal maximum impedance, but high enough to ensure that the ventricle is well past the last contraction. When it is determined that Z is greater than Th(1), the routine goes to 130 and determines whether impedance has dropped below a second predetermined threshold Th(2). The second threshold is chosen as being less than the expected minimum impedance, but sufficiently below Th(1) to indicate that the ventricle is filling with blood and is approaching a substantially filled state. The impedance measurement is taken until Z is determined to be less than Th(2), at which point the pacemaker performs the steps indicated at block 132. Here, the oscillator is stopped, and is not started again until turned on at block 122 in the next cycle, thereby saving energy. Timeout of a short interval D2 is initiated. D2 is a predetermined interval which is programmed to determine the desired time of delivering a pace pulse following detection of impedance becoming less than Th(2). The duration of D2 may be very short, in the range of 5–10 ms, and may be chosen by the physician to provide a pace pulse a bit before the ventricle has completely filled with blood. As indicated at block 134, the ventricular pace is delivered at the timeout of D2.

In the algorithm of FIG. 5, there is provided an effective "window" for impedance measurement, between the timeout of duration D1 and the determination that impedance has dropped below the Th(2) value. In an alternate embodiment, not illustrated, the impedance-measuring oscillator is likewise turned on at the timeout of D1, and the pacemaker likewise checks to see whether impedance is greater than Th(1). However, thereafter, instead of looking for impedance to drop below a predetermined threshold, the pacemaker examines the rate of decrease of impedance, i.e., impedance slope, and initiates timeout of D2 when this slope reaches a predetermined value.

While some illustrative algorithms for determining when is the best time for pacing the ventricle have been illustrated, it is to be understood that these illustrations are only exemplary, and other techniques can be used. The invention is not limited either in terms of the sensor or sensors utilized for measuring ventricular impedance, or the specific algorithms which are utilized for analyzing the sensor data. The important feature is that of determining when the ventricle has filled to a desired point for pacing, and delivering the pace pulse at or about at that moment so as to optimize the cardiac output. For example, other sensors such as pressure and Doppler sensors, can be used. It is also noted that while the invention provides particular enhancement to a single chamber ventricular pacemaker, it also provides improvement to dual chamber pacemakers. Further, the technique of this invention may be used in combination with conventional synchronized pacing and rate responsive pacing techniques.

We claim:

1. A pacing system characterized by having a pulse generator and associated circuitry arranged and disposed to comprise a means for delivering ventricular pace pulses in timed relation to ventricular filling, comprising:

electrode delivery means for delivering said ventricular pace pulses to heart tissue, sensing means for sensing variations in the amount of blood in said ventricle wherein said sensing means comprises impedance measuring means for obtaining a representation of intra-ventricular impedance in said patient's ventricle, and said detection means comprises minima means for detecting when said impedance representation is substantially at a minimum, corresponding to substantial filling of the patient's ventricle;

detection means for detecting from said variations when said ventricle has filled with blood to a desired volume level wherein said detection means comprises window means for establishing a window of a predetermined time interval around a last detected impedance minimum, and means for examining said impedance value within said window in a cycle to determine the impedance minimum for said cycle; and control means for controlling said means for delivering ventricular pulses as a function of detection of filling to said desired level or volume value.

2. A pacing system as set forth in claim 1 said electrode delivery means comprising a lead with distal and proximal ends and having at least one pacing electrode at about said distal end for positioning in a patient's ventricle said at least one pacing electrode being electrically connected through said lead at said proximal end to said pulse generator and associated circuitry.

3. The pacing system as described in claim 2, wherein said impedance measuring means comprises at least one measuring electrode on said lead positioned so as to be in said patient's ventricle.

4. The pacing system as described in claim 2, wherein said impedance measuring means comprises current generating means for generating a current flow within the patient's ventricle, and a pair of electrodes on said lead for measuring voltage corresponding to said current flow.

5. The pacing system as described in claim 2, wherein said detection means comprises means for detecting a predetermined drop in intra-cardiac impedance.

6. The pacing system as described in claim 2, comprising timing means for determining the time interval between respective times of detecting substantial ventricular filling for successive pacemaker cycles, and means for enabling said control means to control delivery of a ventricular pace pulse as a function of detection of a said substantial ventricular filling value only when said time interval is equal to or greater than a predetermined value.

7. The pacing system as described in claim 2, wherein said pulse generator is a dual chamber pacemaker having a second lead with at least one electrode adapted to be positioned in a patient's atrium, wherein said dual chamber pacemaker comprises synchronous means for timing out an AV interval and delivering a ventricular pace pulse upon time-out of said AV interval in the absence of detection that said ventricle has filled with blood to a desired level.

8. The pacing system as described in claim 2, wherein said pulse generator and associated circuitry comprises a single chamber pacemaker and said lead has no atrial electrodes but only one or more electrodes adapted to be positioned only in the patient's ventricle.

9. The pacing system as described in claim 1, wherein said detection means further comprises means for detecting each cycle when detected impedance drops below a predetermined threshold.

10. The pacing system as described in claim 1, wherein said detection means further comprises means for detecting in each cardiac cycle when, following a prior delivered ventricular pace pulse or natural ventricular beat, when said intra-ventricular impedance reaches a substantially minimum value.

11. The pacing system as described in claim 1, wherein said detection means further comprises average means for determining a rolling average of said substantially minimum values, and wherein said control means controls delivery of said ventricular pace pulses as a function of said rolling average or of its change or rate of change.

12. The pacing system of claim 1 wherein said detection means has a controller for determining which cycles will be examined for said impedance.

13. The pacing system as described in claim 1, wherein said control means comprises increment means for controlling said pulse generator to deliver a ventricular pace pulse in a predetermined time increment related to timing of said detecting of a desired level of blood.

14. The pacing system of claim 1 wherein said detection means has a controller for determining which part of examined cycles will be examined for said impedance.

15. The pacing system of claim 1 wherein said detection means has a controller for determining the rate at which a heart cycle's segments will be sampled and thus examined for said impedance.

16. A pacing system for delivering ventricular pace pulses in physiologically timed relation to the filling of a patient's ventricle, comprising:

pace pulse means for generating ventricular pace pulses;

lead means for delivering said generated pace pulses to said patient's ventricle;

sensing means for sensing a measure of the relative amount of blood in said ventricle wherein said sensing means comprises impedance measuring means for obtaining a representation of intraventricular impedance in said patient's ventricle and said processing means determines when change of said impedance indicates that the ventricle has substantially filled with blood and wherein said impedance measuring means comprises current generating means for generating a high frequency current and window means for limiting the generation of said high frequency current to a duration comprising the time of expected impedance change due to the filling of the ventricle with blood;

processing means for processing said measure to determine an indication that such ventricle is filling with blood; and control means responsive to a said indication for controlling said pace pulse means to generate a ventricular pace pulse.

17. The system as described in claim 16, wherein said processing means comprises means for determining when said ventricle is filling with blood at a predetermined rate, and said control means comprises means for timing out a short interval after the time of said filling at a predetermined rate, for controlling delivery of a pace pulse following time out of said short interval.

* * * * *